United States Patent [19]

Nohara

[11] Patent Number: 4,716,167
[45] Date of Patent: Dec. 29, 1987

[54] 2-AMINO-5-OXO-5H-[1]BENZOPYRANO[2,3-B]PYRIDINE-3-CARBOXYLIC ACID DERIVATIVES

[75] Inventor: Akira Nohara, Kyoto, Japan

[73] Assignee: Takeda Chemical Industries, Ltd., Osaka, Japan

[21] Appl. No.: 823,479

[22] Filed: Jan. 28, 1986

[30] Foreign Application Priority Data

Jan. 28, 1985 [JP] Japan .................. 60-15109
Mar. 20, 1985 [JP] Japan .................. 60-56909

[51] Int. Cl.$^4$ .......................................... C07D 491/052
[52] U.S. Cl. .......................................... 514/291; 546/89
[58] Field of Search .......................................... 546/89

[56] References Cited

U.S. PATENT DOCUMENTS 4,143,042  3/1979  Nohara et al. .................. 546/89
4,539,326  9/1985  Nohara et al. .................. 546/89

OTHER PUBLICATIONS

CAS Online Structural Search.

Primary Examiner—Henry R. Jiles
Assistant Examiner—J. Richter
Attorney, Agent, or Firm—Wegner & Bretschneider

[57] ABSTRACT

The present invention relates to novel 2-amino-5-oxo-5H-[1]benzopyrano[2,3-b]pyridine-3-carboxylic acid derivatives useful for prophylaxis and therapy of allergic diseases such as allergic asthma, allergic dermatitis and hay fever, which have the following formula:

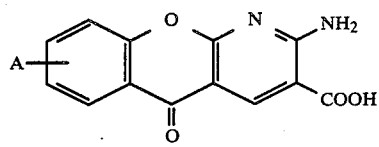

wherein A is

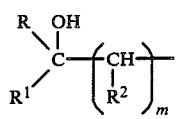

($R$, $R^1$ and $R^2$ are independently hydrogen or lower alkyl and m is 0 or 1, with the proviso that when m is 1, $R^1$ is hydrogen) or R—Co— (R has the same meaning as defined above), or a physiologically acceptable salt thereof, and to a method for preparing the same.

9 Claims, No Drawings

2-AMINO-5-OXO-5H-[1]BENZOPYRANO[2,3-B]PYRIDINE-3-CARBOXYLIC ACID DERIVATIVES

The present invention relates to 2-amino-5-oxo-5 H-[1]benzopyrano[2,3-b]pyridine-3-carboxylic acid derivatives of the formula (I):

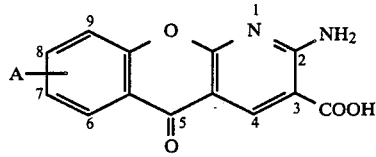
(I)

wherein A is

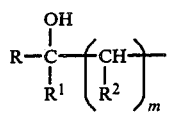

(R, R$^1$ and R$^2$ are independently hydrogen or lower alkyl and m is 0 or 1, with the proviso that when m is 1, R$^1$ is hydrogen) or R—CO—(R has the same meaning as defined above), and their physiologically acceptable salts and to a method for preparing the same.

The compounds of the formula (I) according to the present invention can be produced by subjecting a compound of the formula (II)

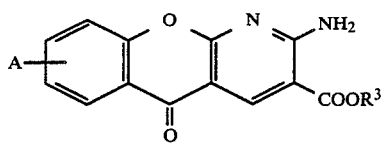
(II)

wherein A is of the same meaning as defined above and R$^3$ is lower alkyl, to hydrolysis.

The compounds of the formula (I) as obtained by the above procedure and their physiologically acceptable salts have an activity of inhibiting liberation of histamine and antiallergic activity useful for prophylaxis and therapy of asthma etc.

Attacks of bronchial asthma are considered to occur by, among others, constriction of bronchial smooth muscle, as well as acceleration of mucus secretion, both due to liberation of chemical mediators such as histamine from mast cells, basophilic cells or the like by antigen-antibody reaction. As a literature reference relating to 2-amino-5-oxo-5H-[1]-benzopyrano[2,3-b]pyridine-3-carboxylic acid derivatives having the activity of inhibiting the liberation of chemical mediators from mast cells etc., U.S. Pat. No. 4,143,042 (Japanese Unexamined Patent Laid-open No. 111096/1978) is mentioned.

It is desirable to further strengthen the activity, lower the toxicity and increase the solubility in water of the compounds of U.S. Pat. No. 4,143,042.

The present inventors undertook further studies for the purpose of finding compounds satisfying the above-mentioned requirements, on which this invention has been predicated.

In the above formulae, the substituent A may be located at any of the 6-, 7-, 8- or 9-position. As the lower alkyl representable by R, R$^1$, R$^2$ and R$^3$ is mentioned (C$_{1-6}$) alkyl, for example, methyl, ethyl, n-propyl, n-butyl, n-pentyl or n-hexyl, practically preferable ones among them being (C$_{1-5}$) alkyl for R, (C$_{1-2}$) alkyl for R$^1$ and (C$_{1-3}$) alkyl for R$^2$ and R$^3$.

The compound (II), wherein A is

or R—CO—, can be produced by allowing a compound of the formula (III);

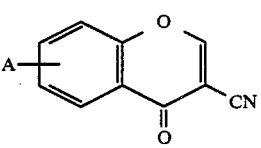
(III)

wherein A is

or R—CO— as defined above, to react with cyanoacetate of the formula (IV)

$$NC-CH_2COOR^3 \quad (IV)$$

wherein R$^3$ has the same meaning as defined above.

The cyanoacetate (IV) is used generally in an amount of about 1–10 moles relative to 1 mole of the compound (III).

The above-mentioned reaction is conducted preferably in the presence of a base. The base is exemplified by organic amines such as primary amine e.g. n-butylamine, benzylamine and aniline; secondary amine e.g. diethylamine, dipropylamine, dibutylamine, piperidine, pyrrolidine and morpholine; tertiary amine e.g. 1,8-diazabicyclo[5,4,0]-7-undecene and triethylamine; and heterocyclic base e.g. imidazole and 2-methylimidazole. These organic bases are used generally in an amount of about catalytic amount to 5 moles relative to 1 mole of the compound (III).

In general, the reaction is conducted preferably in the presence of an organic solvent exemplified by alcohols such as methanol, ethanol, propanol and butanol, aromatic hydrocarbons such as benzene and toluene, or dimethylformamide. While the reaction temperature, time and other conditions are not especially critical, the reaction is usually conducted at temperatures within the range from room temperature to about the boiling point of the solvent then employed for about 1 to 24 hours.

The compound (III), one of the starting materials in the method of this invention, wherein A is

can be produced by allowing a compound of the formula (III-1):

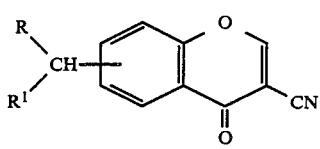

wherein R and $R^1$ are as defined above, to react with N-bromosuccinimide, followed by allowing the resultant to react with an alkaline aqueous solution, the compound (III-1) being known by U.S. Pat. No. 3,896,114 (Japanese Unexamined Patent Laid-open No. 103578/1973 or producible by a method described in said U.S. patent. The compound (III), wherein A is R—CO—(R is lower alkyl), can be produced by subjecting a compound (III), wherein A- is

to the treatment in accordance with the description in the specification of U.S. Pat. No. 4,085,116 (Japanese Patent Publication No. 54150/1983).

The compound (II), wherein A is

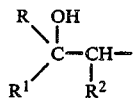

can be prepared by, for example, the reaction steps as shown below:

the reaction temperature ranges generally from 50° C. to around the boiling point of the solvent used.

For accelerating the reaction, photo-irradiation or addition of a radical reaction initiator e.g. benzoyl peroxide is preferable. Then the compound (V) thus obtained is allowed to react with a base such as sodium acetate, potassium acetate, sodium hydroxide and potassium hydroxide to thereby produce a compound (VII). The solvent to be used may be any one which is in common use. Dimethylformamide, water and a mixture of them are preferred examples. The reaction temperature ranges from room temperature to around 100° C.

Or, a compound (V) is subjected to reaction in an acid aqueous solution e.g. an aqueous solution of acetic acid to give a compound (VII). Or, a compound (V) is allowed to react with an alkali to give a compound (VI), which is then allowed to react with an acid such as hydrochloric acid, sulfuric acid and p-toluenesulfonic acid to give a compound (VII). The compound (VII) thus produced is allowed to react with cyanoacetate (IV) in the presence of a base to give a compound (VIII).

These cyanoacetates are practically used in an amount of 1–10 moles per mole of the compound (VII). As the bases to be used for the above reaction there may be mentioned organic amines, for example, primary amines e.g. n-butylamine, benzylamine, aniline, etc., secondary amines e.g. diethylamine, dipropylamine, dibutylamine, piperidine, pyrrolidine, morpholine, etc., tertiary amines such as 1,8-diazabicyclo[5,4,0]-7-undecene and triethylamine, or heterocyclic bases such as imidazole and 2-methylimidazole. The amount of the organic bases to be employed ranges usually from the catalylic amount to 5 moles relative to one mole of the compound (VII).

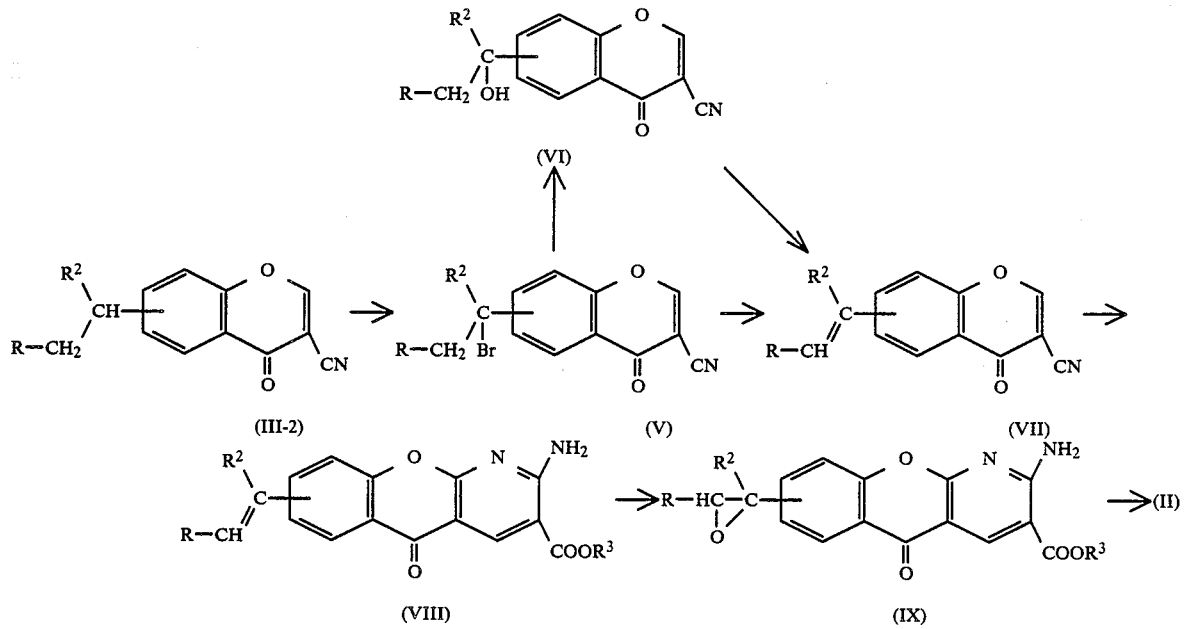

(in each formula, R, $R^2$ and $R^3$ have the same meaning as defined above).

Specifically, a compound (III-2) is allowed to react with 1–3 equivalents of N-bromosuccinimide to yield a compound (V). The solvent to be employed for this reaction is exemplified by chloroform, carbon tetrachloride, dichloromethane and tetrachloroethane, and the reaction temperature ranges generally from 50° C.

The reaction is, in general, preferably conducted in an organic solvent, for example, alcohols such as methanol, ethanol, propanol, butanol, etc., aromatic hydrocarbons such as benzene, toluene, etc., or dimethylformamide, etc. The temperature, time and other conditions of the reaction are not particularly critical, but the reaction is generally carried out at about room temperature to the boiling point of the solvent used for about one hour to 24 hours. By allowing the compound (VIII) thus obtained to react with a peracid such as m-chloroperbenzoic acid and peracetic acid, a compound (IX) can be produced. As examples of the solvents to be employed for the reaction may be mentioned chloroform, dichloromethene, carbon tetrachloride, tetrachloroethane, etc. The reaction temperature is suitably selected from room temperature to about the boiling point of the solvent then used.

Then, by subjecting the compound (IX) to catalytic reduction, the desired starting compound (II) can be produced. As the catalysts employable for the catalytic reduction, conventional ones such as those of palladium type, platinum type, etc. can be mentioned, but, palladium catalyst such as palladium-carbon, etc. is generally used. As the solvent are generally used ethanol, tetrahydrofuran, etc.

On the other hand, the compound (III), wherein A is —CHO, can be produced by a method described on J. Med. Chem. 22, 290 (1979). Specifically stating, this compound (III) can be produced by allowing cyanoacetate (IV) to react with a compound of the formula (III-3);

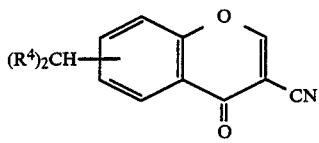
(III-3)

wherein $R^4$ is lower acyloxy e.g. acetoxy or propionyloxy, to give a compound the formula (X);

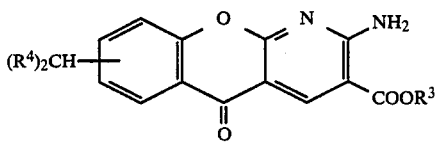
(X)

wherein $R^4$ is as defined above, then by subjecting the compound (X) to mild hydrolysis using e.g. dilute hydrochloric acid.

Hydrolysis of the compound (II) obtained as above gives a compound (I). The hydrolysis is conducted under alkaline or acid conditions. The alkali is exemplified by sodium hydroxide or potassium hydroxide, and the acid is exemplified by sulfuric acid, hydrochloric acid or phosphoric acid. The reaction is carried out usually at about 50–150° C. in the presence of an alcohol such as methanol, ethanol and propanol, or an organic acid such as formic acid and acetic acid. These alkali hydroxides or acids are used in an amount of 1–100 moles relative to 1 mole of the compound (II), and the reaction time ranges usually from one hour to several days.

By allowing a compound (I) to react with an organic amine e.g. ethanolamine, dl-methylephedrine, 1-(3,5-dihydroxyphenyl)-L-isopropylaminoethanol, isoproterenol, dextromethorphan, hetrazan (diethylcarbamazine), diethylamine and thriethylamine, or alkali metal hydroxide e.g. sodium hydroxide and potassium hydroxide, or ammonia by a per se known method, for example, mixing or heating in a proper solvent, the corresponding organic amine salt, alkali metal salt or ammonium salt can be obtained.

The compound (I) or salts thereof prepared thus above have antiallergic activity. Among them, the salts with specific organic amines mentioned as above show especially excellent antiallergic actions, which are useful as prophylactic and therapeutic agents against allergic diseases such as allergic asthma, allergic dermatitis and hay fever. Further, alkali metal salts and organic amine salts thereof have good solubility in water, and their aqueous solutions are stable and convenient for formulation into various preparations including injections and solutions.

When the compounds (I) or salts thereof are used, for example, as prophylactic and therapeutic agents against the above-mentioned allergic diseases, they can be administered, orally as tablets, capsules, powders and solutions usually in a daily dose of about 1-500 mg per adult, besides, in such dosage forms as injections, inhalants and ointments.

The following Reference Examples and Working Examples illustrate the present invention in more detail.

REFERENCE EXAMPLE b 1

In carbon tetrachloride (300 ml) was suspended 6-isopropyl-4-oxo-4H-1-benzopyran-3-carbonitrile (10.65 g). To the suspension was added N-bromosuccinimide (8.90 g). The mixture was subjected to reflux for two hours under irradiation of infrared ray lamp (Toshiba, 100 V, 375 WR). The resultant was then cooled to room temperature, followed by removal of insolubles by filtration. The filtrate was concentrated under reduced pressure. The concentrate was dissolved in ethyl acetate (150 ml), which was washed with water three times, dried and concentrated. The precipitating crystals were collected by filtration to give 6-(1-bromo-1-methylethyl)-4-oxo-4H-1-benzopyran-3-carbonitrile as colorless prisms (7.0 g). Melting point: 115°–117° C.

REFERENCE EXAMPLE 2

In 1N sodium hydroxide (250 ml) was dissolved 6-(1-bromo-1-methylethyl)-4-oxo-4H-1-benzopyran-3-carbonitrile (9.6 g). The solution was stirred at room temperature for 2 hours, then cooled and acidified with concentrated hydrochloric acid. The resultant was subjected to extraction with ethyl acetate (200 ml×3), washed with water and dried (sodium sulfate). Ethyl acetate was then evaporated off, and the residue was subjected to a silica-gel (200 g) column chromatography using chloroform-acetone-formic acid (90:10:1) as the eluent. From the eluate was evaporated off the solvent. To the residue was added ethanol, which was left standing overnight. The resulting precipitates were collected by filtration to give crystals (4.36 g) of 6-(1-hydroxy-1-methylethyl)-4-oxo-4H-1-benzopyran-3-carbonitrile, recrystallization of which from ethanol gave colorless plates, m.p. 166°–167° C.

REFERENCE EXAMPLE 3

To a mixture of 6-(1-hydroxy-1-methylethyl)-4-oxo-4H-1-benzopyran-3-carbonitrile (4.7 g), ethyl cyanoacetate (2.5 g) and ethanol (100 ml) was added piperidine (1.9 g), which was refluxed for 3 hours, then cooled. The precipitating crystals were collected by filtration. The crystals were dissolved in chloroform, which was subjected to a silica-gel (120 g) column chromatography using chloroform-acetone-formic acid (90:10:1) as the eluent. The solvent was evaporated off. To the residue was added ethanol, and sparingly soluble matter was collected by filtration, which was recrystallized from chloroform to give colorless needles (4.86 g) of ethyl 2-amino-7-(1-hydroxy-1-methylethyl)-5-oxo-5H-[1]benzopyrano[2,3-b]pyridine-3-carboxylate, m.p. 263°-264° C.

REFERENCE EXAMPLE 4

In ethanol (800 ml) was suspended 6-acetyl-4-oxo-4H-1-benzopyran-3-carbonitrile (32 g). To the suspension were added ethyl cyanoacetate (23.9 ml) and piperidine (23.7 ml). The mixture was refluxed for one hour, then cooled to room temperature. The resulting crystals were collected by filtration, washed with ethanol, then with acetone, followed by drying to give ethyl 7-acetyl-2-amino-5-oxo-5H-[1]benzopyrano[2,3-b]pyridine-3-carboxylate as yellow crystals (46.3 g). Melting point: >300° C.

REFERENCE EXAMPLE 5

A mixture of 6-(1-bromo-1-methylethyl)-4-oxo-4H-1-benzopyran-3-carbonitrile (2.0 g), acetic acid (20 ml) and water (5 ml) was heated at 100° C. for one hour, which was then concentrated. The concentrate was subjected to a silica-gel (100 g) column-chromatography, eluting with chloroform-acetone-formic acid (20:1:0.1). The initial eluate was recrystallized from ethanol to give colorless crystals (600 mg) of 6-isopropenyl-4-oxo-4H-1-benzopyran-3-carbonitrile, m.p. 142°-144° C.

REFERENCE EXAMPLE 6

A mixture of 6-(1-bromo-1-methylethyl)-4-oxo-4H-1-benzopyran-3-carbonitrile (2.0 g), sodium acetate (575 mg) and dimethylformamide (20 ml) was heated for one hour, which was then concentrated. The concentrate was dissolved in chloroform. The solution was washed with water and dried (sodium sulfate), followed by removing chloroform by evaporation. The residue was subjected to a silica-gel (100 g) column chromatography, eluting with chloroform-acetone-formic acid (20:1:0.1). The initial eluate was recrystallized from ethanol to give colorless crystals (1.07 g) of 6-isopropenyl-4-oxo-4H-1-benzopyran-3-carbonitrile, m.p. 142°-144° C.

REFERENCE EXAMPLE 7

A mixture of 6-isopropenyl-4-oxo-4H-1-benzopyran-3-carbonitrile (800 mg), ethanol (40 ml), piperidine (0.6 ml) and ethyl cyanoacetate (0.7 ml) was subjected to reflux for three hours, which was then left standing at room temperature overnight. Precipitating crystals were collected by filtration, which were recrystallized from ethanol to afford colorless crystals (1.09 g) of ethyl 2-amino-7-isopropenyl-5-oxo-5H-[1]benzopyrano[2,3-b]pyridine-3-carboxylate, m.p. 227°-230° C. (decomp.).

REFERENCE EXAMPLE 8

A mixture of ethyl 7-isopropenyl-5-oxo-5H-1-benzopyrano[2,3-b]pyridine-3-carboxylate (400 mg), m-chloroperbenzoic acid (340 mg) and chloroform (20 ml) was subjected to reflux for one hour, which was washed with water, 10% aqueous solution of sodium hydrosulfite, and water in that order. The chloroform layer was dried (sodium sulfate). Chloroform was evaporated off, and the residue was purified by a silica-gel (50 g) chromatography using as the eluent chloroform-acetone-formic acid (20:1:0.1). The initial eluate was recrystallized from chloroform to yield colorless crystals (230 mg) of ethyl 2-amino-7-(1,2-epoxy-1-methylethyl)-5-oxo-5H-[1]benzopyrano[2,3-b]pyridine-3-carboxylate. This product did not show a precise melting point.

NMR(CDCl$_3$)δ: 1.41(3H, t, J=7 Hz), 1.79(3H, s), 2.83(1H, d, J=5 l Hz), 3.03(1H, d, J=5 Hz), 4.40(2H, q, J=7 Hz), 5.95(1H, br), 7.45(1H, d, J=9 Hz), 7.70(1H, dd, J=2 and 9 Hz), 8.27(1H, d, J=2 Hz), 8.35(1H, br), 9.14(1H, s).

REFERENCE EXAMPLE 9

A mixture of ethyl 2-amino-7-(1,2-epoxy-1-methylethyl)-5-oxo-5H-[1]benzopyrano[2,3-b]pyridine-3-carboxylate (800 mg), 5% palladium-carbon (700 mg), ethanol (50 ml) and tetrahydrofuran (150 ml) was subjected to catalytic reduction for two hours at room temperature under ordinary pressure. Then, the catalyst was filtered off, and the filtrate was concentrated to dryness. The concentrate was purified by means of a silica-gel (80 g) column chromatography using chloroform-acetone-formic acid (9:1:0.1). The solvent was evaporated off, and the residue was recrystallized from chloroform to yield colorless prisms (499 mg) of ethyl 2-amino-7-(2hydroxy-1-methylethyl)-5-oxo-5H-[1]benzopyrano[2,3-b]-pyridine-3-carboxylate, m.p. 255°-256° C.

EXAMPLE 1

A suspension consisting of ethyl 2-amino-7-(1-hydroxy-1-methylethyl)-5-oxo-5H-[1]benzopyrano[2,3-b]-pyridine-3-carboxylate (37.3 g), ethanol (2.3 l) and 0.5N sodium hydroxide (620 ml) was stirred at 50° C. for 2 hours, then ethanol was evaporated off. The concentrate was acidified with hydrochloric acid (pH 3-4), then the resulting precipitates were collected by filtration and washed with water, followed by recrystallization from dimethylformamide-water. The crystals were washed with ethanol to give 2-amino-7-(1-hydroxy-1-methylethyl)-5-oxo-5H-[1]benzopyrano[2,3-b]-pyridine-3-carboxylic acid (32.5 g).

NMR(DMSO-d$_6$)δ: 1.53(6H, s), 5.12 (1H, m), 7.50(1H, d, J=9 Hz), 7.92(1H, dd, J=2 and 9 Hz), 8.20(1H, d, J=2 Hz), 8.20(2H, m), 8.85(1H, s), 13.38(1H, m).

IR $\nu_{max}^{nujol}$cm$^-$:3450, 3320, 1680, 1665, 1610, 1535, 1230, 1220, 1160, 1120, 830 790.

EXAMPLE 2

In ethanol (3 l) was suspended ethyl 7-acetyl-2-amino-5-oxo-5H-[1]benzopyrano[2,3-b]pyridine-3-carboxylate (46 g). To the suspension were added water (460 ml) and 1N sodium hydroxide (462 ml). The mixture was stirred at room temperature for 1.5 hour, then at 50°-55° C. for 2 hours. The precipitating crystals were collected by filtration, and washed with ethanol. The crystals thus obtained were suspended in warm water (about 2 l). To the suspension was added concentrated hydrochloric acid (20 ml), and the mixture was stirred for 20 minutes. Insoluble matter was collected by filtration, washed with water, followed by recrystallization from dimethylformamide-water to give 7-acetyl-2-amino-5-oxo-5H-[1]benzopyrano[2,3-b]pyridine-3-carboxylic acid as colorless crystals (39.3 g). Melting point: >300° C.

EXAMPLE 3

A mixture of ethyl 2-amino-7-(2-hydroxy-1-methylethyl)-5-oxo-5H-[1]benzopyrano[2,3-b]pyridine-3-carboxylate (480 mg), ethanol (40 ml), water (5 ml) and 1N sodium hydroxide (5 ml) was heated at 50° C. for 80 minutes, which was then concentrated. The concentrate was dissolved in water, which was made acid with 10% hydrochloric acid. Resulting precipitates were collected by filtration, washed with water, and recrystallized from dimethylformamide-ethanol-water to yield colorless crystals (386 mg) of 2-amino-7-(2-hydroxy-1-methylethyl)-5-oxo-5H-[1]benzopyrano-[2,3-b]pyridine-3-carboxylic acid, m.p. >300° C.

What we claim is:

1. A compound of the formula:

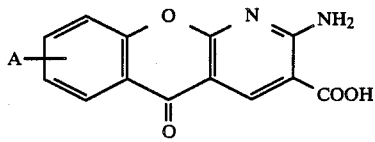

wherein A is

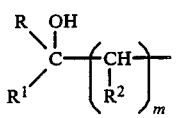

(R, $R^1$ and $R^2$ are independently hydrogen or lower alkyl and m is 0 or 1, with the proviso that when m is 1, $R^1$ is hydrogen) or R—CO— (R has the same meaning as defined above), or a physiologically acceptable salt thereof.

2. A compound as claimed in claim 1, wherein A is

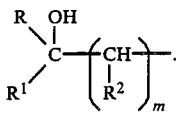

3. A compound as claimed in claim 1, wherein A is R—CO—.

4. A compound as claimed in claim 2, wherein m is 1.

5. A compound as claimed in claim 2, wherein m is 0.

6. A compound as claimed in claim 1, wherein R and $R^1$ are lower alkyl, and m is 0.

7. A compound as claimed in claim 1, wherein the compound is 2-amino-7-(1-hydroxy-1-methylethyl)-5-oxo-5H-[1]benzopyrano[2,3-b]pyridine-3-carboxylic acid.

8. A compound as claimed in claim 1, wherein the compound is 7-acetyl-2-amino-5-oxo-5H-[1]benzopyrano[2,3-b]pyridine-3-carboxylic acid.

9. A compound as claimed in claim 1, wherein the compound is 2-amino-7-(2-hydroxy-1-methylethyl)-5-oxo-5H-[1]benzopyrano[2,3-b]pyridine-3-carboxylic acid.

* * * * *